(12) United States Patent
Coates et al.

(10) Patent No.: US 10,888,575 B2
(45) Date of Patent: Jan. 12, 2021

(54) COMBINATION COMPRISING ZIDOVUDINE AND A CARBAPENEM

(71) Applicant: HELPERBY THERAPEUTICS LIMITED, London (GB)

(72) Inventors: Anthony Coates, London (GB); Yanmin Hu, London (GB)

(73) Assignee: HELPERBY THERAPEUTICS LIMITED

( * ) Notice: Subject to any disclaimer, the term of this patent is extended or adjusted under 35 U.S.C. 154(b) by 3 days.

(21) Appl. No.: 16/317,512

(22) PCT Filed: Jul. 11, 2017

(86) PCT No.: PCT/GB2017/052030
§ 371 (c)(1),
(2) Date: Jan. 11, 2019

(87) PCT Pub. No.: WO2018/011562
PCT Pub. Date: Jan. 18, 2018

(65) Prior Publication Data
US 2019/0321384 A1    Oct. 24, 2019

(30) Foreign Application Priority Data
Jul. 12, 2016    (GB) .................................. 1612093.3

(51) Int. Cl.
| *A61K 31/7072* | (2006.01) |
| *A61P 31/04* | (2006.01) |
| *A61K 31/407* | (2006.01) |
| *A61K 38/12* | (2006.01) |

(52) U.S. Cl.
CPC ........ *A61K 31/7072* (2013.01); *A61K 31/407* (2013.01); *A61K 38/12* (2013.01); *A61P 31/04* (2018.01)

(58) Field of Classification Search
CPC .................................................. A61K 31/7072
See application file for complete search history.

(56) References Cited

FOREIGN PATENT DOCUMENTS

| WO | 00/28074 A1 | 5/2000 |
| WO | 0205850 | 1/2002 |
| WO | 2005/014585 A1 | 2/2005 |
| WO | 2014/147405 A1 | 9/2014 |
| WO | 2015/114340 A1 | 8/2015 |

OTHER PUBLICATIONS

Pankey et al., Diagn. Microbiol. Infect. Dis., 2009, vol. 63, pp. 228-232 (Year: 2009).*
Daoud et al., Open Journal of Medical Microbiology, 2013, vol. 3, pp. 253-258 (Year: 2013).*
Fan et al., PLoS ONE, Jun. 17, 2016, vol. 11, No. 6, e0157757 (Year: 2016).*
Dickstein et al., BMJ Open, Apr. 20, 2016, vol. 6, e009956 (Year: 2016).*
Coates et al., "The future challenges facing the development of new antimicrobial drugs," Nature Reviews, Drug Discovery, 2002, 1(11), pp. 895-910.
Doleans-Jordheim et al., "Zidovudine (AZT) has a bactericidal effect on enterobacteria and induces genetic modifications in resistant strains," Eur J Clin Microbiol Infect Dis., Oct. 2011; 30(10), pp. 1249-1256.
Herrmann et al., "Intracellular activity of zidovudine (3'-azido-3'-deoxythymidine, AZT) against *Salmonella typhimurium* in the macrophage cell line J774-2," Antimicrobial Agents Chemotherapy, May 1992, 36(5), pp. 1081-1085.
Hu and Coates, "Enhancement by novel anti-methicillin-resistant *Staphylococcus aureus* compound HT61 of the activity of neomycin, gentamicin, mupirocin and chlorhexidine: in vitro and in vivo studies," Journal Antimicrobial Chemotherapy, Feb. 2013, vol. 68, pp. 374-384.
Orhan et al., "Synergy tests by E test and checkerboard methods of antimicrobial combinations against *Brucella melitensis*," J. Clin. Microbiol., 2005, 43(1), pp. 140-143.
Papp-Wallace et al., "Carbapenems: Past, Present, and Future," Antimicrobial Agents Chemotherapy, 2011, 55(11), pp. 4943-4960.
"Remington: The Science and Practice of Pharmacy", Lippincott Williams and Wilkins, 21.Sup.St. Edition, 2005.
Smith et al., "Validation of a High-Throughput Screening Assay for Identification of Adjunctive and Directly Acting Antimicrobials Targeting Carbapenem-Resistant Enterobacteriaceae." Assay and Drug Development Technologies. vol. 14, No. 3, 2016, pp. 194-206.

* cited by examiner

*Primary Examiner* — Rei Tsang Shiao
(74) *Attorney, Agent, or Firm* — McDonald Hopkins LLC

(57) ABSTRACT

The invention provides a combination comprising zidovudine or a pharmaceutically acceptable derivative thereof and a carbapenem or a pharmaceutically acceptable derivative thereof, optionally with a polymyxin selected from polymyxin E and polymyxin or a pharmaceutically acceptable derivative thereof. This combination is particularly useful for the treatment of microbial infections.

13 Claims, 3 Drawing Sheets

BAA2471

BAA2469

BAA2470

COMBINATION COMPRISING ZIDOVUDINE AND A CARBAPENEM

CROSS-REFERENCE TO RELATED APPLICATION

This application is a 35 U.S.C. § 371 national stage filing of PCT Application No. PCT/GB2017/052030 filed on Jul. 11, 2017, which claims priority to Great Britain Patent Application No. 1612093.3 filed on Jul. 12, 2016, each of which are incorporated herein in their entirety by reference.

FIELD OF THE INVENTION

The present invention relates to the combination of zidovudine or a pharmaceutically acceptable derivative thereof with a carbapenem or a pharmaceutically acceptable derivative thereof, and optionally a polymyxin selected from polymyxin E and polymyxin B, or a pharmaceutically acceptable derivative thereof. The present invention also relates to the use of these combinations for the treatment of microbial infections. In particular, it relates to the use of such combinations to kill multiplying or clinically latent microorganisms associated with microbial infections, e.g. Gram-negative bacterial infections.

BACKGROUND

Zidovudine (AZT) is a nucleoside analogue reverse-transcriptase inhibitor, a type of antiretroviral drug which is used for the treatment of HIV/AIDS infection. As well as its antiretroviral activity against HIV, the antibacterial effect of zidovudine (AZT) has been demonstrated both in vitro and in vivo with experimental models of gram-negative bacteria infections (Hermann et al., Antimicrob Agents Chemther. 1992 May; 36(5): 1081-1085).

There have also been reports of zidovudine being active as an anti-microbial when combined with gentamicin. Doléans-Jordheim A. et al., for example disclosed that zidovudine (AZT) had a bactericidal effect on some enterobacteria, yet could induce resistance in *Escherichia coli* (Eur J Clin Microbiol Infect Dis. 2011 October; 30(10):1249-56). These resistances were associated with various modifications in the thymidine kinase gene. Furthermore, an additive or synergistic activity between AZT and the two aminoglycoside antibiotics amikacin and gentamicin was observed against enterobacteria.

International Patent Application published as WO2014/147405 describes the use of zidovudine in combination with a polymyxin selected from colistin and polymyxin B for treating a microbial infection. International Patent Application published as WO2015/114340 describes the use of zidovudine in combination with a polymyxin selected from colistin or polymyxin B, an anti-tuberculosis antibiotic selected from rifampicin, rifapentine or rifabutin and optionally piperine, for treating a microbial infection.

Carbapenems are antibiotics used for the treatment of infections known or suspected to be caused by multidrug-resistant (MDR) bacteria. Like penicillin and cephalosporin, they are members of the beta lactam class of antibiotics, which kill bacteria by binding to penicillin-binding proteins and inhibiting cell wall synthesis. Unlike cephalosporins and penicillin, however, the carbapenems exhibit a broad spectrum of activity and have greater potency again Gram-positive and Gram-negative bacteria. They are therefore often used as a last resort when patients with infections become severely ill or are suspected of harboring resistant bacteria (*Antimicrob. Agents Chemother.*, 55, 4943-4960 (2011)). Unfortunately, however, several studies show that resistance to carbapenems is increasing throughout the world.

Carbapenems which have been approved for clinical use include imipenem, meropenem, ertapenem, doripenem, panipenem/betamipron and biapenem. Other carbapenems include razupenem, tebipenem, lenapenem, tomopenem and thienpenem. Meropenem is marketed under the trade names Optinem and Meronem in Europe. Both products include the active ingredient meropenem trihydrate.

In view of the problem of bacterial resistance and the importance of antimicrobial agents such as carbapenems and polymyxins in the fight against bacterial infection, the identification of compounds capable of enhancing the antimicrobial activity of such agents addresses an important need.

International Patent Application published as WO2000/028074 describes a method of screening compounds to determine their ability to kill log phase (i.e. multiplying) and/or clinically latent microorganisms. Using this method, the Applicant has observed that many known compounds, including the antiretroviral drug zidovudine, have a synergistic effect with carbapenems or pharmaceutically acceptable derivatives thereof, such as meropenem, and optionally a polymyxin selected from polymyxin E and polymyxin B, or pharmaceutically acceptable derivatives thereof, against multiplying and/or clinically latent microorganisms.

The present invention is based on the unexpected finding that the combination of zidovudine or a pharmaceutically acceptable derivative thereof, and a carbapenem or a pharmaceutically acceptable derivative thereof (e.g. meropenem or a pharmaceutically acceptable derivative thereof), and optionally a polymyxin selected from polymyxin E and polymyxin B, or a pharmaceutically acceptable derivative thereof exhibits synergistic antimicrobial activity against log phase (i.e. multiplying) and/or clinically latent microorganisms. Particularly against log phase bacteria. In other words, the combination(s) has a greater biological activity than the expected additive effect of each agent at the stated dosage level. The surprising biological activity of the combinations of the present invention offers the opportunity to shorten chemotherapy regimens and may result in a reduction in the emergence of microbial resistance associated with the use of such combinations.

Synergy in the context of antimicrobial drugs is measured in a number of ways that conform to the generally accepted opinion that "synergy is an effect greater than additive". One of the ways to assess whether synergy has been observed is to use the "chequerboard" technique. This is a well-accepted method that leads to the generation of a value called the fractional inhibitory concentration index (FICI). Orhan et al J. Clin. Microbiol. 2005, 43(1):140 describes the chequerboard method and analysis in the paragraph bridging pages 140-141, and explains that the FICI value is a ratio of the sum of the MIC (Minimum Inhibitory Concentration) level of each individual component alone and in the mixture. The combination is considered synergistic when the $\Sigma$FIC is $\leq 0.5$, indifferent when the $\Sigma$FIC is $>0.5$ but $<4.0$, and antagonistic when the $\Sigma$FIC is $>4.0$.

Another accepted test for ascertaining the presence or absence of synergy is to use time-kill methods. This involves the dynamic effect of a drug combination being compared to each drug alone when assessing the effect on bacterial log or stationary-growth over time. Again, the possible results are for synergistic, additive or antagonistic effects.

SUMMARY OF THE INVENTION

Thus, in one embodiment the present invention provides a combination of zidovudine or a pharmaceutically acceptable derivative thereof and a carbapenem or a pharmaceutically acceptable derivative thereof, optionally with a polymyxin selected from polymyxin E and polymyxin B, or a pharmaceutically acceptable derivative thereof. Preferably the carbapenem is meropenem or a pharmaceutically derivative thereof.

In one embodiment the combination includes a polymyxin such that the combination may be described as a "triple combination". Preferably the polymyxin is polymyxin E or a pharmaceutically acceptable derivative thereof. Most preferred is colistimethate sodium.

In another embodiment the present invention provides the use of zidovudine or a pharmaceutically acceptable derivative thereof in combination with a carbapenem or a pharmaceutically acceptable derivative thereof, optionally with a polymyxin selected from polymyxin E and polymyxin B, or a pharmaceutically acceptable derivative thereof, in the manufacture of a medicament for treating a microbial infection.

In another embodiment the present invention provides the use of a carbapenem or a pharmaceutically acceptable derivative thereof in combination with zidovudine or a pharmaceutically acceptable derivative thereof, optionally with a polymyxin selected from polymyxin E and polymyxin B, or a pharmaceutically acceptable derivative thereof.

In one embodiment the afore-mentioned uses include a polymyxin, preferably polymyxin E or a pharmaceutically acceptable derivative thereof.

Additionally the present invention provides the combination of zidovudine or a pharmaceutically acceptable derivative thereof and a carbapenem or a pharmaceutically acceptable derivative thereof, optionally with a polymyxin selected from polymyxin E and polymyxin B, or a pharmaceutically acceptable derivative thereof, for use in the treatment of a microbial infection, preferably for use in the treatment of a bacterial infection. In one embodiment the combination includes a polymyxin, preferably polymyxin E or a pharmaceutically acceptable derivative thereof.

In a further embodiment, the invention provides a method of treating a microbial infection which comprises administering to a mammal, including man, zidovudine or a pharmaceutically acceptable derivative thereof in combination with a carbapenem or a pharmaceutically acceptable derivative thereof, optionally with a polymyxin selected from polymyxin E and polymyxin B, or a pharmaceutically acceptable derivative thereof. In one embodiment the method includes administering a polymyxin, preferably polymyxin E or a pharmaceutically acceptable derivative thereof.

There is also provided a pharmaceutical composition comprising zidovudine or a pharmaceutically acceptable derivative thereof in combination with a carbapenem or a pharmaceutically acceptable derivative thereof, optionally with a polymyxin selected from polymyxin E and polymyxin B, or a pharmaceutically acceptable derivative thereof, and a pharmaceutically acceptable adjuvant, diluent or carrier. In one embodiment the pharmaceutical composition is for use in the treatment of a microbial infection, preferably wherein the microbial infection is a bacterial infection. In a further embodiment the pharmaceutical composition includes a polymyxin, preferably polymyxin E or a pharmaceutically acceptable derivative thereof.

In a further embodiment, the invention relates to a product comprising zidovudine or a pharmaceutically acceptable derivative thereof and a carbapenem or a pharmaceutically acceptable derivative thereof, optionally with a polymyxin selected from polymyxin E and polymyxin B, or a pharmaceutically acceptable derivative thereof, as a combined preparation for simultaneous, separate or sequential use in killing multiplying and/or clinically latent microorganisms associated with a microbial infection. Preferably for killing multiplying bacteria associated with a bacterial infection. In one embodiment the product includes a polymyxin, preferably polymyxin E or a pharmaceutically acceptable derivative thereof.

DETAILED DESCRIPTION OF THE INVENTION

Figure 1:
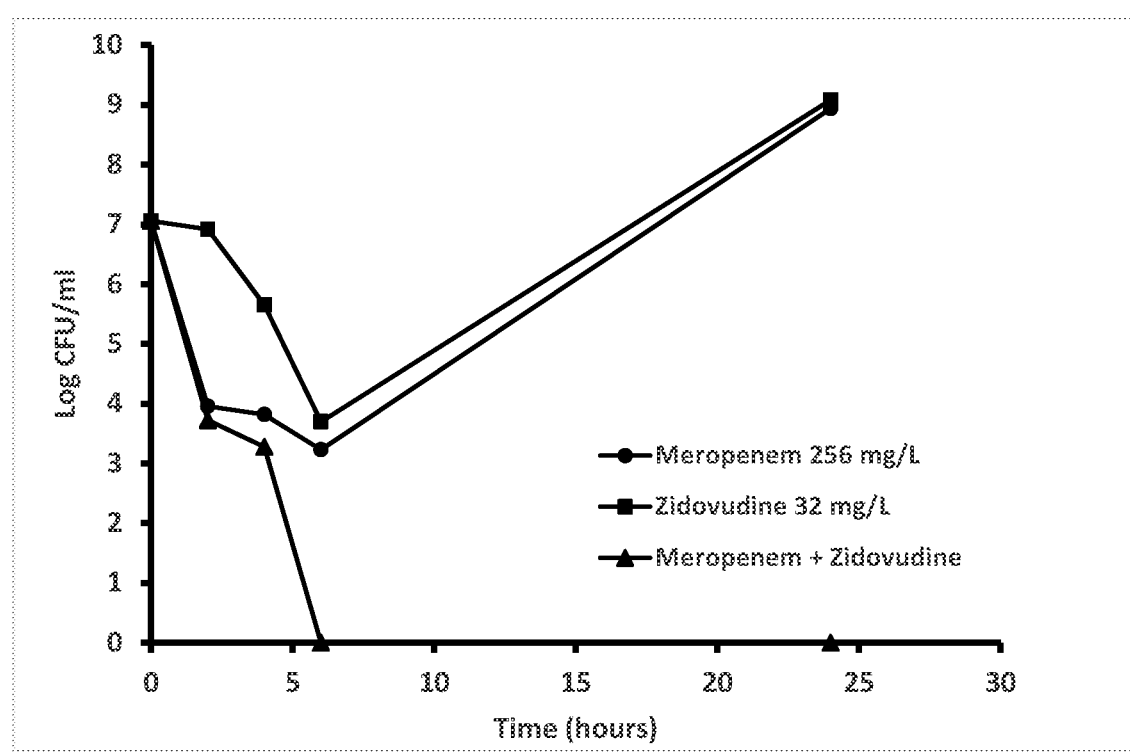
FIG. 1 is a time-kill curve (Log CFU/ml against time (hours)) showing the antimicrobial activity of meropenem at a concentration of 256 mg/L, zidovudine at a concentration of 32 mg/L and the combination of meropenem (256 mg/L) and zidovudine (32 mg/L) against log phase NDM-1 *E. coli* (BAA2471).

As described below, the combinations of the present invention have been demonstrated to be particularly effective against drug-resistant bacteria, particularly drug-resistant Gram-negative bacteria, opening the way for said combinations to be administered both to drug-resistant strains and in said strains before drug-resistance is built up, i.e. as a first line treatment.

As used herein, the term "in combination with" covers both separate and sequential administration of the agents. When the agents are administered sequentially, either the zidovudine or the carbapenem or the optional polymyxin may be administered first. When administration is simultaneous, the agents may be administered either in the same or a different pharmaceutical composition. Adjunctive therapy, i.e. where one agent is used as a primary treatment and the other agent(s) is used to assist that primary treatment, is also an embodiment of the present invention.

The combinations of the present invention may be used to treat microbial infections. In particular they may be used to kill multiplying and/or clinically latent microorganisms associated with microbial infections, preferably multiplying microorganisms associated with microbial infections, e.g. multiplying bacteria associated with Gram-negative bacterial infections. References herein to the treatment of a microbial infection therefore include killing multiplying and/or clinically latent microorganisms associated with such infections.

As used herein, "kill" means a loss of viability as assessed by a lack of metabolic activity.

As used herein, "clinically latent microorganism" means a microorganism that is metabolically active but has a growth rate that is below the threshold of infectious disease expression. The threshold of infectious disease expression refers to the growth rate threshold below which symptoms of infectious disease in a host are absent.

The metabolic activity of clinically latent microorganisms can be determined by several methods known to those skilled in the art; for example, by measuring mRNA levels in the microorganisms or by determining their rate of uridine uptake. In this respect, clinically latent microorganisms, when compared to microorganisms under logarithmic growth conditions (in vitro or in vivo), possess reduced but still significant levels of:

(I) mRNA (e.g. from 0.0001 to 50%, such as from 1 to 30, 5 to 25 or 10 to 20%, of the level of mRNA); and/or (II) uridine (e.g. [$^3$H]uridine) uptake (e.g. from 0.0005 to 50%, such as from 1 to 40, 15 to 35 or 20 to 30% of the level of [$^3$H]uridine uptake).

Clinically latent microorganisms typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction. In addition, clinically latent microorganisms are phenotypically tolerant, and as such are sensitive (in log phase) to the biostatic effects of conventional antimicrobial agents (i.e. microorganisms for which the minimum inhibitory concentration (MIC) of a conventional antimicrobial is substantially unchanged); but possess drastically decreased susceptibility to drug-induced killing (e.g. microorganisms for which, with any given conventional antimicrobial agent, the ratio of minimum microbiocidal concentration (e.g. minimum bactericidal concentration, MBC) to MIC is 10 or more).

As used herein, the term "microorganisms" means fungi and bacteria. References herein to "microbial", "antimicrobial" and "antimicrobially" shall be interpreted accordingly. For example, the term "microbial" means fungal or bacterial, and "microbial infection" means any fungal or bacterial infection.

In one embodiment of the invention, one or more of the aforementioned combinations is used to treat a bacterial infection, in particular the combinations may be used to kill multiplying and/or clinically latent microorganisms associated with a bacterial infection. As used herein, the term "bacteria" (and derivatives thereof, such as "microbial infection") includes, but is not limited to, references to organisms (or infections due to organisms) of the following classes and specific types:

Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*); Streptococci (e.g. beta-haemolytic, pyogenic streptococci (such as *Strept. agalactiae, Strept. canis, Strept. dysgalactiae dysgalactiae, Strept. dysgalactiae equisimilis, Strept. equi equi, Strept. equi zooepidemicus, Strept. iniae, Strept. porcinus* and *Strept pyogenes*), microaerophilic, pyogenic streptococci (*Streptococcus* "milleri", such as *Strept. anginosus, Strept. constellatus constellatus, Strept. constellatus pharyngidis* and *Strept intermedius*), oral streptococci of the "*mitis*" (alpha-haemolytic—*Streptococcus* "*viridans*", such as *Strept. mitis, Strept. oralis, Strept. sanguinis, Strept. cristatus, Strept. gordonii* and *Strept. parasanguinis*), "*salivarius*" (non-haemolytic, such as *Strept. salivarius* and *Strept vestibularis*) and "*mutans*" (tooth-surface streptococci, such as *Strept. criceti, Strept. mutans, Strept. ratti* and *Strept. sobrinus*) groups, *Strept. acidominimus, Strept. bovis, Strept. faecalis, Strept. equinus, Strept. pneumoniae* and *Strept. suis*, or Streptococci alternatively classified as Group A, B, C, D, E, G, L, P, U or V *Streptococcus*);

Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri*; Bacillaceae, such as *Bacillus anthracis, Bacillus subtilis, Bacillus thuringiensis, Bacillus stearothermophilus* and *Bacillus cereus*; Enterobacteriaceae, such as *Escherichia coli, Enterobacter* (e.g. *Enterobacter aerogenes, Enterobacter agglomerans* and *Enterobacter cloacae*), *Citrobacter* (such as *Citrob. freundii* and *Citrob. divernis*), *Hafnia* (e.g. *Hafnia alvei*), *Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri, Shigella boydii* and *Shigella sonnei*), *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*), *Proteus* (e.g. *Pr. mirabilis, Pr. rettgeri* and *Pr. vulgaris*), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*); Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*); *Helicobacter* (e.g. *Helicobacter pylori, Helicobacter cinaedi* and *Helicobacter fennelliae*); *Acinetobacter* (e.g. *A. baumanii, A. calcoaceticus, A. haemolyticus, A. johnsonii, A. junii, A. lwoffi* and *A. radioresistens*); *Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzeri*); *Bacteroides fragilis*; *Peptococcus* (e.g. *Peptococcus niger*); *Peptostreptococcus*; *Clostridium* (e.g. *C. perfringens, C. difficile, C. botulinum, C. tetani, C. absonum, C. argentinense, C. baratii, C. bifermentans, C. beijerinckii, C. butyricum, C. cadaveris, C. camis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tertium*); *Mycoplasma*

(e.g. *M. pneumoniae, M. hominis, M. genitalium* and *M. urealyticum*); Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium mucogenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*); Haemophilus (e.g. *Haemophilus influenzae, Haemophilus ducreyi, Haemophilus aegyptius, Haemophilus parainfluenzae, Haemophilus haemolyticus* and *Haemophilus parahaemolyticus*); Actinobacillus (e.g. *Actinobacillus actinomycetemcomitans, Actinobacillus equuli, Actinobacillus hominis, Actinobacillus lignieresii, Actinobacillus suis* and *Actinobacillus ureae*); Actinomyces (e.g. *Actinomyces israelii*); Brucella (e.g. *Brucella abortus, Brucella canis, Brucella melintensis* and *Brucella suis*); Campylobacter (e.g. *Campylobacter jejuni, Campylobacter coli, Campylobacter lari* and *Campylobacter fetus*); *Listeria monocytogenes*; Vibrio (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*); *Erysipelothrix rhusopathiae*; Corynebacteriaceae (e.g. *Corynebacterium diphtheriae, Corynebacterium jeikeum* and *Corynebacterium urealyticum*); Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*); Pasteurella (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida* septica, *Pasteurella pneumotropica* and *Pasteurella stomatis*); Bordetella (e.g. *Bordetella bronchiseptica, Bordetella hinzii, Bordetella holmseii, Bordetella parapertussis, Bordetella pertussis* and *Bordetella trematum*); Nocardiaceae, such as *Nocardia* (e.g. *Nocardia asteroides* and *Nocardia brasiliensis*); Rickettsia (e.g. *Ricksettsii* or *Coxiella burnetii*); Legionella (e.g. *Legionalla anisa, Legionalla birminghamensis, Legionalla bozemanii, Legionalla cincinnatiensis, Legionalla dumoffii, Legionalla feelefi, Legionalla gormanii, Legionalla hackeliae, Legionalla israelensis, Legionalla jordanis, Legionalla lansingensis, Legionalla longbeachae, Legionalla maceachernii, Legionalla micdadei, Legionalla oakridgensis, Legionalla pneumophila, Legionalla sainthelensi, Legionalla tucsonensis* and *Legionalla wadsworthii*); *Moraxella catarrhalis; Cyclospora cayetanensis; Entamoeba histolytica; Giardia lamblia; Trichomonas vaginalis; Toxoplasma gondii; Stenotrophomonas maltophilia; Burkholderia cepacia; Burkholderia mallei* and *Burkholderia pseudomallei; Francisella tularensis;* Gardnerella (e.g. *Gardneralla vaginalis* and *Gardneralla mobiluncus*); *Streptobacillus moniliformis*; Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*); Bartonella (*Bartonella baciffiformis, Bartonella clarridgeiae, Bartonella elizabethae, Bartonella henselae, Bartonella quintana* and *Bartonella vinsonii arupensis*); Leptospira (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*); Spirillium (e.g. *Spirillum minus*); Baceteroides (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*); Prevotella (e.g. *Prevotella bivia, Prevotella buccae, Prevotella corporis, Prevotella dentalis* (*Mitsuokella dentalis*), *Prevotella denticola, Prevotella disiens, Prevotella enoeca, Prevotella heparinolytica, Prevotella intermedia, Prevotella loeschfi, Prevotella melaninogenica, Prevotella nigrescens, Prevotella oralis, Prevotella oris, Prevotella oulora, Prevotella tannerae, Prevotella venoralis* and *Prevotella zoogleoformans*); Porphyromonas (e.g. *Porphyromonas asaccharolytica, Porphyromonas cangingivalis, Porphyromonas canons, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*); Fusobacterium (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);

Chlamydia (e.g. *Chlamydia trachomatis*); Cryptosporidium (e.g. *C. parvum, C. hominis, C. canis, C. felis, C. meleagridis* and *C. muris*); Chlamydophila (e.g. *Chlamydophila abortus* (*Chlamydia psittaci*), *Chlamydophila pneumoniae* (*Chlamydia pneumoniae*) and *Chlamydophila psittaci* (*Chlamydia psittaci*)); Leuconostoc (e.g. *Leuconostoc citreum, Leuconostoc cremoris, Leuconostoc dextranicum, Leuconostoc lactis, Leuconostoc mesenteroides* and *Leuconostoc pseudomesenteroides*); Gemella (e.g. *Gemella bergeri, Gemella haemolysans, Gemella morbillorum* and *Gemella sanguinis*); and Ureaplasma (e.g. *Ureaplasma parvum* and *Ureaplasma urealyticum*).

Preferably, the bacterial infections treated by the combinations described herein are Gram-negative bacterial infections. Particular Gram-negative bacteria that may be treated using a combination of the invention include:

Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*); *Haemophilis influenzae*; Mycobacteria, such as *Mycobacterium tuberculosis*; and *Enterobacter* (e.g. *Enterobacter cloacae*). Preferably, the bacteria are Enterobacteriaceae, such as *Escherichia coli* and *Klebsiella* (e.g. *Klebs. pneumoniae* and *Klebs. oxytoca*). Particularly preferred are *Escherichia coli,* and *Klebs. pneumoniae* (e.g. *Klebs. pneumoniae* subsp. *pneumoniae*).

In all embodiments it is preferable that the combination therapy is synergistic as compared to the administration of the combination components taken alone.

The combination of the present invention is particularly beneficial in treating (multi)-drug-resistant ((M)DR) bacteria. With respect to Enterobacteriaceae, drug resistance most often builds up to carbapenemase i.e. carbapenemase-resistant strains and "extended spectrum β-lactamase" (ESBL) strains for example New Delhi Metallo-beta-lactamase-1 (NDM-1) resistant *Klebs.* Pneumonia, and NDM-1 *E. coli*.

It should be kept in mind that although a combination such as that claimed may initially be demonstrated to be functional in treating (M)DR strains, they can then be used in treating non-resistant strains. This is especially valuable in the context of the presently claimed combination where the primary therapy for Enterobacteriaceae, such as *Escherichia coli*, and *Klebsiella* (e.g. *Klebs. pneumoniae* and *Klebs. oxytoca*) are antimicrobial drugs that are expensive due to prevailing patent protection. The replacement of such "ethical" drugs by a combination of "generic" antibiotics is thought to be beneficial from a therapeutic perspective as well as financial/economic perspective in times where governments are seeking to reduce the cost of healthcare.

The combinations of the present invention may be used to treat infections associated with any of the above-mentioned bacterial organisms, and in particular they may be used for killing multiplying and/or clinically latent microorganisms associated with such an infection, e.g. a Gram-negative bacterial infection.

Particular conditions which may be treated using the combination of the present invention include those which are caused by Gram-negative bacteria such as abscesses, asthma, bacilliary dysentry, bacterial conjunctivitis, bacterial keratitis, bacterial vaginosis, bone and joint infections, bronchitis (acute or chronic), brucellosis, burn wounds, cat scratch fever, cellulitis, chancroid, cholangitis, cholecystitis, cystic fibrosis, cystitis, nephritis, diffuse panbronchiolitis, dental caries, diseases of the upper respiratory tract, empymea, endocarditis, endometritis, enteric fever, enteritis, epididymitis, epiglottitis, eye infections, furuncles, gardnerella vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leptospirosis, listeriosis, liver abscesses, Lyme disease, lymphogranuloma venerium, mastitis, mastoiditis, meningitis and infections of the nervous system, non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, pleural effusion, pneumonia, postoperative wound infections, post-operative gas gangrene, prostatitis, pseudo-membranous colitis, psittacosis, pyelonephritis, Q fever, rat-bite fever, Ritter's disease, salmonellosis, salpingitis, septic arthritis, septic infections, septicameia, systemic infections, tonsillitis, trachoma, typhoid, urethritis, urinary tract infections, wound infections; or infections with, *Escherichia coli, Klebs. pneumoniae, Klebs. oxytoca, Pr. mirabilis, Pr. rettgeri, Pr. vulgaris, Haemophilis influenzae, Enterococcus faecalis, Enterococcus faecium,* and *Enterobacter cloacae*.

It will be appreciated that references herein to "treatment" extend to prophylaxis as well as the treatment of established diseases or symptoms.

As used herein the term "pharmaceutically acceptable derivative" means:

(a) pharmaceutically acceptable salts; and/or
(b) solvates (including hydrates).

Suitable acid addition salts include carbon/late salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalene-sulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

Zidovudine has the systematic (IUPAC) name of 1-[(2R, 4S, 5S)-4-Azido-5-(hydroxymethyl)oxolan-2-yl]-5-methylpyrimidine-2,4-dione, and is available by prescription under the trade name Retrovir®. It is also known as 3'-azido-3'-deoxythymidine and has the following chemical structure:

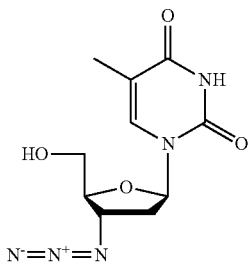

References herein to a carbapenem mean a compound with the following core chemical structure:

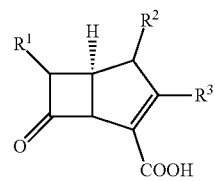

where $R^1$, $R^2$ and $R^3$ are different substituents. The carbapenem may be selected from the group consisting of imipenem, meropenem, ertapenem, doripenem, panipenem, biapenem, razupenem, tebipenem, lenapenem, tomopenem and thienpenem or a pharmaceutically derivative thereof, e.g. meropenem trihydrate. These compounds have the following chemical structures, including the above chemical core.
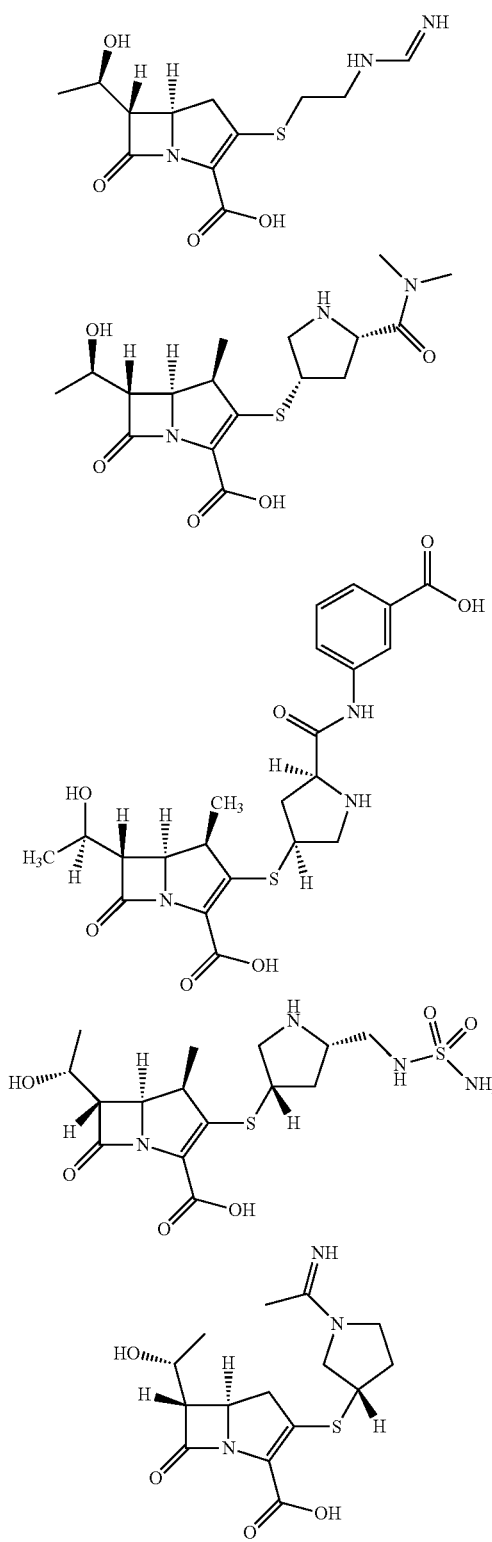
-continued
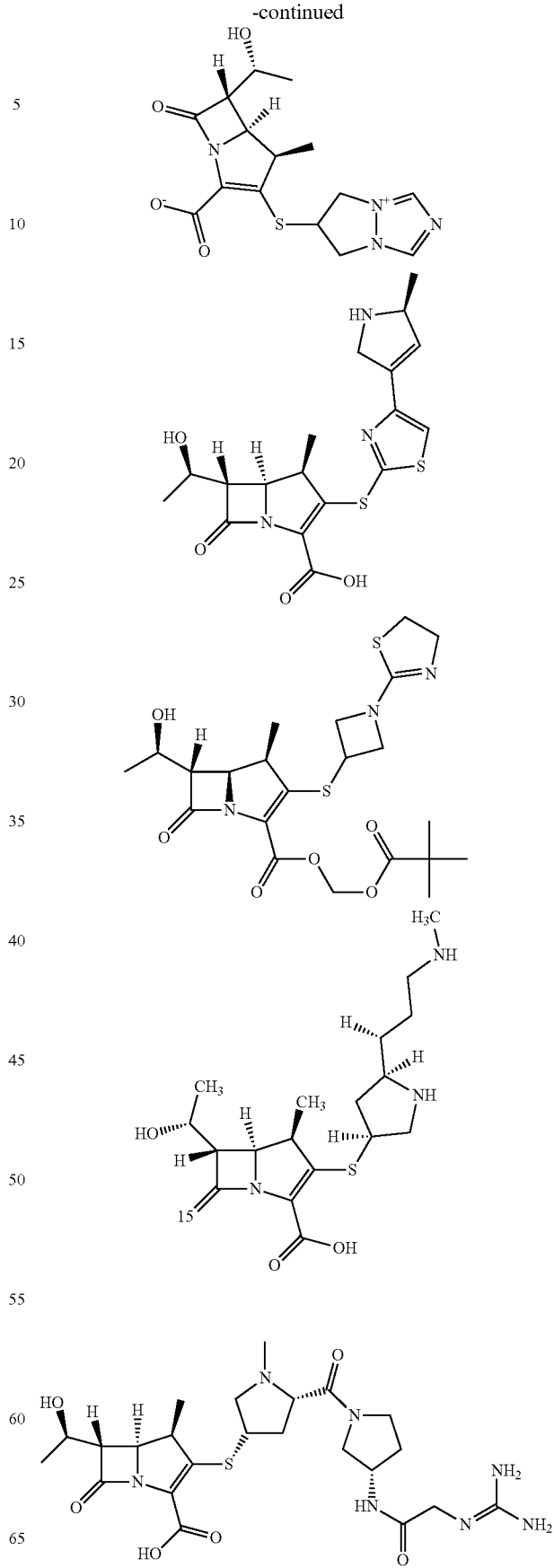

-continued

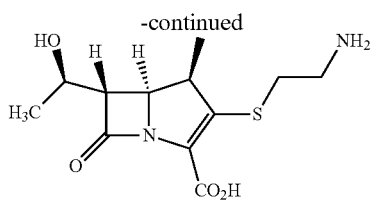

Preferably the carbapenem is selected from the group consisting of imipenem, meropenem, ertapenem, doripenem, panipenem and biapenem, or a pharmaceutically acceptable derivative thereof. More preferably the carbapenem is selected from meropenem, imipenem and ertapenem or a pharmaceutically acceptable derivative thereof. Most preferably the carbapenem is meropenem or a pharmaceutically acceptable derivative thereof, e.g. meropenem trihydrate.

The polymyxin is selected from polymyxin E and polymyxin B, or a pharmaceutically acceptable derivative thereof. Polymixin E is also known as colistin. For example the polymyxin may be selected from colistin sulfate, colistimethate sodium, colistin sodium methanesulfonate, or polymyxin B sulfate. Particularly preferred is colistin, colistin sulfate, colistin sodium methane sulfonate or colistimethate sodium, e.g. colistin or colistimethate sodium.

Colistin (polymyxin E) is an antibiotic produced by certain strains of the bacteria *Paenibacillus polymyxa*. Colistin has the following chemical structure and the IUPAC chemical name N-(4-amino-1-(1-(4-amino-1-oxo-1-(3,12,23-tris(2-aminoethyl)-20-)1-hydroxyethyl)-6,9-diisobutyl-2,5,8,11,14,19,22-heptaoxo-1,4,7,10,13,18-exaazacyclotricosan-15-ylamino)butan-2-ylamino)-3-hydroxybutan-2-ylamino)-1-oxobutan-2-yl)-N,5-dimethylheptanamide.

the two compounds must be stable and compatible with each other and the other components of the formulation.

Formulations of the invention include those suitable for oral, parenteral (including subcutaneous e.g. by injection or by depot tablet, intrathecal, intramuscular e.g. by depot and intravenous), and rectal or in a form suitable for administration by inhalation or insufflation administration. The most suitable route of administration may depend upon the condition and disorder of the patient. Preferably, the compositions of the invention are formulated for parenteral administration. More preferably the compositions of the invention are formulated for intravenous or intramuscular administration.

The formulations may conveniently be presented in unit dosage form and may be prepared by any of the methods well known in the art of pharmacy e.g. as described in "*Remington: The Science and Practice of Pharmacy*", Lippincott Williams and Wilkins, $21^{st}$ Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% (such as from 3 to 50%) for liquid preparations.

Formulations suitable for oral administration may be presented as discrete units such as capsules, cachets or

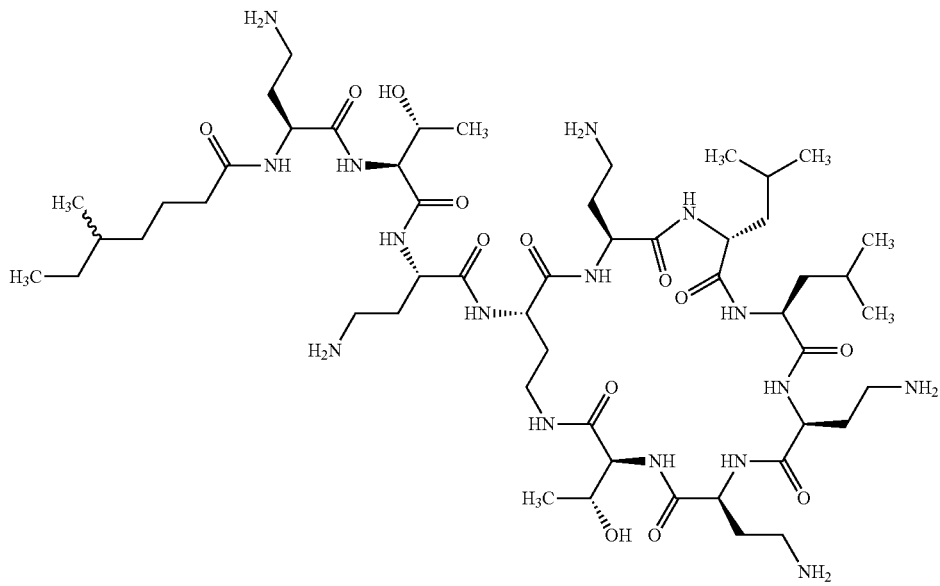 [SMILES: CCC(C)CCCC(=O)N[C@@H](CCN)C(=O)N[C@H](C(=O)N[C@@H](CCN)C(=O)N[C@H]1CCNC(=O)[C@H]([C@@H](C)O)NC(=O)[C@H](CCN)NC(=O)[C@H](CCN)NC(=O)[C@H](CC(C)C)NC(=O)[C@@H](CC(C)C)NC(=O)[C@H](CCN)NC1=O)[C@@H](C)O]

Compounds for use according to the invention may be administered as the raw material but the active ingredients are preferably provided in the form of pharmaceutical compositions.

The active ingredients may be used either as separate formulations or as a single combined formulation. When combined in the same formulation it will be appreciated that tablets (e.g. chewable tablets in particular for paediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or molding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Molded tablets may be made by molding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Combinations for use according to the invention may be presented in a pack or dispenser device which may contain one or more unit dosage forms containing the active ingredients. The pack may, e.g. comprise metal or plastic foil, such as a blister pack. Where the compositions are intended for administration as two separate compositions these may be presented in the form of a twin pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

The compounds for use in the combination of the present invention are commercially available or can be prepared by synthesis methods known in the art. Zidovudine, imipenem, imipenem monohydrate, meropenem, mereopenem trihydrate, ertapenem, ertapenem sodium, doripenem hydrate, doripenem monohydrate, biapenem, colistin sulfate, colistin sodium methanesulfonate and colistimethate sodium are for example available from Sigma-Aldrich®.

Suitable dosages and formulations for the administration of zidovudine are described in the product label for Retrovir® oral solution or capsules which can be found at http://www.medicines.org.uk/emc/medicine/12444/SPC/Retrovir+250 mg+Capsules/

Suitable dosages and formulations for the administration of imipenem are described in the product label for imipenem/cilastatin 500 mg/500 mg powder for solution for infusion which can be found at https://www.medicines.org.uk/emc/medicine/24538; and the product label for Primaxin IV injection which can be found at https://www.medicines.org.uk/emc/medicine/7456.

Suitable dosages and formulations for the administration of meropenem are described in the product label for Meronem IV which can be found at https://www.medicines.org.uk/emc/medicine/11215; or in the product label for Meropenem 1 g Powder for Solution for Injection or Infusion found at https://www.medicines.org.uk/emc/medicine/24151.

Meropenem is administered intravenously. It is supplied as a white crystalline powder to be dissolved in 5% monobasic potassium phosphate solution.

Suitable dosages and formulations for the administration of ertapenem are described in the product label for INVANZ® 1 g powder for concentrate for solution for infusion which can be found at https://www.medicines.org.uk/emc/medicine/10421.

Suitable dosages and formulations for the administration of colistin or pharmaceutically acceptable derivatives thereof are known in the art. A suitable dosage and formulation for colistin sulfate is for instance described in the product label for Colomyxin® which can be found at http://www.medicines.org.uk/emc/medicine/6301/SPC/Colomycin+Tablets/. A suitable dosage and formulation for colistimethate sodium is described in the product label for colistimethate sodium 1 Million I.U. Powder for Solution for Injection which can be found at https://www.medicines.org.uk/emc/medicine/23413.

The administration of the combination of the invention by means of a single patient pack, or patients packs of each composition, including a package insert directing the patient to the correct use of the invention is a desirable feature of this invention.

According to a further embodiment of the present invention there is provided a patient pack comprising at least one active ingredient of the combination according to the invention and an information insert containing directions on the use of the combination of the invention.

In another embodiment of the invention, there is provided a double pack comprising in association for separate administration, an antimicrobial agent, preferably having biological activity against clinically latent microorganisms, and one or more of the compounds disclosed herein preferably having biological activity against clinically latent microorganisms.

The amount of active ingredients required for use in treatment will vary with the nature of the condition being treated and the age and condition of the patient, and will ultimately be at the discretion of the attendant physician or veterinarian. In general however, doses employed for adult human treatment will typically be in the range of 0.02 to 5000 mg per day, preferably 1 to 1500 mg per day. The desired dose may conveniently be presented in a single dose or as divided doses administered at appropriate intervals, e.g. as two, three, four or more sub-doses per day.

Biological Tests

Test procedures that may be employed to determine the biological (e.g. bactericidal or antimicrobial) activity of the active ingredients include those known to persons skilled in the art for determining:

(a) bactericidal activity against clinically latent bacteria; and (b) antimicrobial activity against log phase bacteria.

In relation to (a) above, methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound.

By way of example, WO2000028074 describes a suitable method of screening compounds to determine their ability to kill clinically latent microorganisms. A typical method may include the following steps:
(1) growing a bacterial culture to stationary phase;
(2) treating the stationery phase culture with one or more antimicrobial agents at a concentration and or time sufficient to kill growing bacteria, thereby selecting a phenotypically resistant sub-population;
(3) incubating a sample of the phenotypically resistant subpopulation with one or more test compounds or agents; and
(4) assessing any antimicrobial effects against the phenotypically resistant subpopulation.

According to this method, the phenotypically resistant sub-population may be seen as representative of clinically latent bacteria which remain metabolically active in vivo and which can result in relapse or onset of disease.

In relation to (b) above, methods for determining activity against log phase bacteria include a determination, under standard conditions (i.e. conditions known to those skilled in the art, such as those described in WO 2005014585, the disclosures of which document are hereby incorporated by reference), of Minimum Inhibitory Concentration ("MIC") or Minimum Bactericidal Concentration ("MBC") for a test compound. Specific examples of such methods are described below.

EXAMPLES

Example 1: In Vitro Synergistic Effect of Zidovudine and Meropenem Against Log Phase NDM-1 *Klebsiella pneumoniae* Subsp. *Pneumoniae* Using the Chequerboard Method The chequerboard method used in Example 1 followed the protocols detailed in Antimicrob Chemo (2013) 68, 374-384.

Log phase growth of NDM-1 *Klebsiella pneumoniae* subsp. *pneumoniae* was carried out as described in the art. Zidovudine and meropenem were obtained from commercially available sources. The effects of the combination of the present invention were examined by calculating the fractional inhibitory concentration index (FICI) of each combination, as follows:

(MIC of drug A, tested in combination)/(MIC of drug A, tested alone)+(MIC of drug B, tested in combination)/(MIC of drug B, tested alone).

The interaction of the combination was defined as showing synergy if the FICI was ≤0.5, no interaction if the FICI was >0.5 but <4.0 and antagonism if the FICI was >4.0.

| | | | | | | Meropenem | | | | | | | |
|---|---|---|---|---|---|---|---|---|---|---|---|---|---|
| BAA2472 | | 256 | 128 | 64 | 32 | 16 | 8 | 4 | 2 | 1 | 0.5 | 0.25 | 0 |
| zidovudine | 32 | 0.05 | 0.04 | 0.05 | 0.05 | 0.05 | 0.05 | 0.05 | 0.05 | 0.05 | 0.05 | 0.04 | 0.26 0.02 |
| | 16 | 0.05 | 0.04 | 0.04 | 0.04 | 0.05 | 0.05 | 0.04 | 0.05 | 0.05 | 0.04 | 0.18 | 0.04 |
| | 8 | 0.04 | 0.04 | 0.04 | 0.04 | 0.05 | 0.05 | 0.09 | 0.07 | 0.18 | 0.08 | 0.15 | 0.23 |
| | 4 | 0.04 | 0.04 | 0.05 | 0.11 | 0.05 | 0.10 | 0.20 | 0.21 | 0.18 | 0.19 | 0.18 | 0.23 |
| | 2 | 0.05 | 0.05 | 0.05 | 0.06 | 0.07 | 0.16 | 0.20 | 0.21 | 0.12 | 0.09 | 0.16 | 0.10 |
| | 1 | 0.06 | 0.05 | 0.05 | 0.06 | 0.14 | 0.15 | 0.16 | 0.15 | 0.11 | 0.16 | 0.17 | 0.22 |
| | 0.5 | 0.05 | 0.07 | 0.05 | 0.12 | 0.16 | 0.17 | 0.13 | 0.12 | 0.14 | 0.14 | 0.13 | 0.16 |
| | 0 | 0.05 | 0.20 | 0.21 | 0.25 | 0.44 | 0.44 | 0.34 | 0.35 | 0.45 | 0.41 | 0.40 | 0.47 |

The FICI was equal to 0.02 indicating that zidovudine and meropenem have a synergistic effect when used in combination against log phase NDM-1 *Klebsiella pneumoniae* subsp. *pneumoniae*.

Example 2: In Vitro Synergistic Effect of Zidovudine in Combination with Meropenem Against Log Phase NDM-1 *Escherichia coli*

The objective of this example was to test the synergistic effect of zidovudine and meropenem in combination against log phase NDM-1 *Escherichia coli* (BAA2471) and log phase NDM-1 *Escherichia coli* (BAA2469) by time-kill methods over a time period of 24 hours. As described hereinabove, time-kill methods are another accepted test for ascertaining the presence or absence of synergy, and involve comparing the dynamic effect of a drug combination with each drug alone when assessing the effect on bacterial log or stationary-growth over time. The results can either show that the drug combination is synergistic, additive or antagonistic. Such a result is not predictable from the activity of either drug alone or in combination with another agent.

Materials and Methods
1. Bacterial strain used: BAA2471 or BAA2469 strain of *Escherichia coli*
2. Growth of bacteria: Log phase growth of BAA2471 or BAA2469 was carried out according to known methods in the art, e.g. SOP R-005-00 Log Phase Growth of Bacteria.
3. Compound preparation: zidovudine and mereopenem were both obtained from commercial sources (e.g. Sigma-Aldrich).
4. The overnight culture was diluted with nutrient broth (Oxoid) to $10^7$ CFU/ml and 280 μl and 290 μl of the culture was added to each combination well and drug respectively, to make the final concentration of 300 μl.
5. Incubation of the compounds with the bacterial suspension was carried out for 24 hours. At 0, 2, 4, 7 and 24 hours, CFU counts were performed to measure the kill effects of the drug combination.

Results and Discussion

Figure 2:
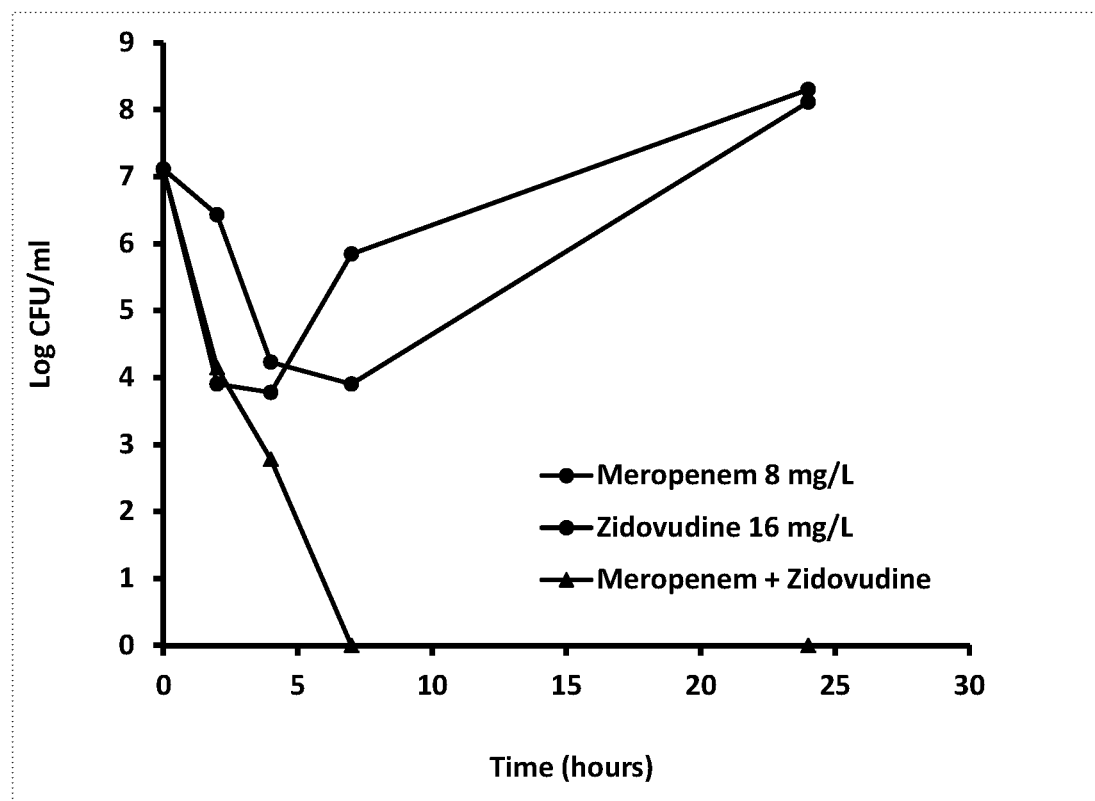
FIG. 2 is a time-kill curve (Log CFU/ml against time (hours)) showing the antimicrobial activity of meropenem at a concentration of 8 mg/L, zidovudine at a concentration of 16 mg/L, and the combination of meropenem (8 mg/L) and zidovudine (16 mg/L) against log phase NDM-1 *E. coli* (BAA2469).

The results are shown in FIG. 1 and FIG. 2. It can be seen from FIG. 1 that zidovudine used alone at a concentration of 32 mg/L and meropenem used alone at a concentration of 256 mg/L had little or no effect against log phase NDM-1 *E.*

*coli*. When used in combination, however, a significant synergistic effect can be seen: complete, long term kill of bacteria occurs at 6 hours. Similarly it can be seen from FIG. 2 that zidovudine used alone at a concentration of 16 mg/L and meropenem used alone at a concentration of 8 mg/L had little or no effect against log phase NDM-1 *E. coli*. When used in combination, however, a significant synergistic effect can be seen. Complete, long term kill of bacteria occurs at 6 hours. In view of the lack of activity for each of the drugs alone, the synergy seen for the combination of zidovudine and a carbapenem according to the claimed invention is a surprising and advantageous technical effect for the treatment of microbial infections.

Example 3: In Vitro Synergistic Effect of Zidovudine, Meropenem and Colistimethate Sodium (CMS) Against Log Phase NDM-1 *Klebsiella pneumoniae* Using the Chequerboard Method The chequerboard method used in Example 1 was followed, according to the protocols detailed in Antimicrob Chemo (2013) 68, 374-384. The bacterial strain of NDM-1 *Klebsiella pneumoniae* was BAA2470. Log phase growth of BAA2470 was carried out as described in the art. Zidovudine, meropenem and colistimethate sodium were obtained from commercially available sources. The effects of the triple combination of the present invention were examined by calculating the MIC for each drug alone and in combination.

The chequerboards are set out below for various concentrations of zidovudine:

| | | | | | | | Colistimethate Sodium | | | | | | | |
|---|---|---|---|---|---|---|---|---|---|---|---|---|---|---|
| | μg/ml | 32 | 16 | 8 | 4 | 2 | 1 | 0.5 | 0.25 | 0.125 | 0.063 | 0.031 | 0 | μg/ml Zidovudine |
| Meropenem | 512 | 0.05 | 0.05 | 0.05 | 0.04 | 0.04 | 0.04 | 0.05 | 0.05 | 0.05 | 0.04 | 0.05 | 0.05 | 0 |
| | 256 | 0.05 | 0.04 | 0.04 | 0.04 | 0.04 | 0.04 | 0.05 | 0.04 | 0.04 | 0.05 | 0.05 | 0.05 | |
| | 128 | 0.05 | 0.04 | 0.04 | 0.04 | 0.17 | 0.21 | 0.30 | 0.24 | 0.26 | 0.29 | 0.33 | 0.36 | |
| | 64 | 0.05 | 0.05 | 0.05 | 0.12 | 0.20 | 0.22 | 0.22 | 0.20 | 0.23 | 0.35 | 0.40 | 0.55 | |
| | 32 | 0.05 | 0.05 | 0.04 | 0.23 | 0.22 | 0.22 | 0.22 | 0.22 | 0.24 | 0.30 | 0.43 | 0.63 | |
| | 16 | 0.04 | 0.04 | 0.05 | 0.24 | 0.24 | 0.24 | 0.24 | 0.25 | 0.24 | 0.31 | 0.45 | 0.70 | |
| | 8 | 0.05 | 0.04 | 0.12 | 0.35 | 0.25 | 0.25 | 0.25 | 0.26 | 0.28 | 0.30 | 0.41 | 0.69 | |
| | 0 | 0.05 | 0.23 | 0.42 | 0.42 | 0.46 | 0.47 | 0.51 | 0.50 | 0.58 | 0.61 | 0.66 | 0.78 | |

| | | | | | | | Colistimethate Sodium | | | | | | | |
|---|---|---|---|---|---|---|---|---|---|---|---|---|---|---|
| | μg/ml | 32 | 16 | 8 | 4 | 2 | 1 | 0.5 | 0.25 | 0.125 | 0.063 | 0.031 | 0 | μg/ml Zidovudine |
| Meropenem | 812 | 0.05 | 0.05 | 0.04 | 0.04 | 0.04 | 0.04 | 0.05 | 0.04 | 0.05 | 0.05 | 0.05 | 0.05 | 0.25 |
| | 256 | 0.05 | 0.04 | 0.04 | 0.04 | 0.04 | 0.05 | 0.05 | 0.05 | 0.05 | 0.05 | 0.05 | 0.05 | |
| | 128 | 0.05 | 0.05 | 0.04 | 0.04 | 0.05 | 0.10 | 0.12 | 0.12 | 0.13 | 0.13 | 0.14 | 0.24 | |
| | 64 | 0.05 | 0.04 | 0.04 | 0.04 | 0.05 | 0.11 | 0.11 | 0.10 | 0.12 | 0.13 | 0.16 | 0.25 | |
| | 32 | 0.04 | 0.04 | 0.04 | 0.05 | 0.05 | 0.07 | 0.08 | 0.08 | 0.08 | 0.09 | 0.13 | 0.25 | |
| | 16 | 0.05 | 0.04 | 0.05 | 0.05 | 0.06 | 0.07 | 0.07 | 0.08 | 0.09 | 0.09 | 0.14 | 0.23 | |
| | 8 | 0.04 | 0.04 | 0.05 | 0.05 | 0.10 | 0.10 | 0.10 | 0.10 | 0.10 | 0.11 | 0.13 | 0.26 | |
| | 0 | 0.05 | 0.04 | 0.05 | 0.11 | 0.11 | 0.15 | 0.22 | 0.15 | 0.15 | 0.17 | 0.20 | 0.31 | |

| | | | | | | | Colistimethate Sodium | | | | | | | |
|---|---|---|---|---|---|---|---|---|---|---|---|---|---|---|
| | μg/ml | 32 | 16 | 8 | 4 | 2 | 1 | 0.5 | 0.25 | 0.125 | 0.063 | 0.031 | 0 | μg/ml Zidovudine |
| Meropenem | 512 | 0.05 | 0.04 | 0.04 | 0.04 | 0.04 | 0.04 | 0.04 | 0.04 | 0.05 | 0.05 | 0.05 | 0.05 | 0.50 |
| | 256 | 0.05 | 0.04 | 0.05 | 0.04 | 0.04 | 0.05 | 0.05 | 0.04 | 0.04 | 0.05 | 0.05 | 0.05 | |
| | 128 | 0.05 | 0.04 | 0.04 | 0.05 | 0.05 | 0.05 | 0.07 | 0.06 | 0.05 | 0.06 | 0.06 | 0.07 | |
| | 64 | 0.05 | 0.04 | 0.04 | 0.04 | 0.05 | 0.06 | 0.08 | 0.06 | 0.05 | 0.06 | 0.09 | 0.09 | |
| | 32 | 0.04 | 0.04 | 0.04 | 0.05 | 0.05 | 0.08 | 0.08 | 0.06 | 0.10 | 0.09 | 0.12 | 0.16 | |
| | 16 | 0.04 | 0.04 | 0.05 | 0.05 | 0.06 | 0.06 | 0.08 | 0.06 | 0.06 | 0.06 | 0.08 | 0.12 | |
| | 8 | 0.04 | 0.04 | 0.05 | 0.05 | 0.06 | 0.06 | 0.06 | 0.08 | 0.07 | 0.17 | 0.09 | 0.14 | |
| | 0 | 0.05 | 0.04 | 0.04 | 0.09 | 0.06 | 0.06 | 0.09 | 0.28 | 0.14 | 0.11 | 0.13 | 0.17 | |

| Colistimethate Sodium | | | | | | | | | | | | | |
|---|---|---|---|---|---|---|---|---|---|---|---|---|---|
| µg/ml | 32 | 16 | 8 | 4 | 2 | 1 | 0.5 | 0.25 | 0.125 | 0.063 | 0.031 | 0 | µg/ml Zidovudine |
| Meropenem 612 | 0.05 | 0.05 | 0.04 | 0.04 | 0.04 | 0.04 | 0.04 | 0.04 | 0.04 | 0.05 | 0.05 | 0.05 | 1 |
| 256 | 0.04 | 0.04 | 0.04 | 0.04 | 0.04 | 0.04 | 0.04 | 0.04 | 0.04 | 0.05 | 0.05 | 0.05 | |
| 128 | 0.05 | 0.04 | 0.04 | 0.04 | 0.05 | 0.05 | 0.05 | 0.04 | 0.04 | 0.05 | 0.05 | 0.05 | |
| 64 | 0.04 | 0.04 | 0.04 | 0.04 | 0.04 | 0.05 | 0.05 | 0.05 | 0.05 | 0.05 | 0.05 | 0.05 | |
| 32 | 0.04 | 0.04 | 0.04 | 0.04 | 0.04 | 0.04 | 0.05 | 0.05 | 0.05 | 0.05 | 0.05 | 0.05 | |
| 16 | 0.04 | 0.04 | 0.04 | 0.04 | 0.05 | 0.05 | 0.05 | 0.05 | 0.06 | 0.07 | 0.08 | 0.09 | |
| 8 | 0.04 | 0.04 | 0.04 | 0.05 | 0.05 | 0.05 | 0.05 | 0.05 | 0.06 | 0.08 | 0.11 | 0.14 | |
| 0 | 0.05 | 0.04 | 0.04 | 0.06 | 0.07 | 0.06 | 0.05 | 0.08 | 0.14 | 0.44 | 0.15 | 0.11 | |

| Colistimethate Sodium | | | | | | | | | | | | | |
|---|---|---|---|---|---|---|---|---|---|---|---|---|---|
| µg/ml | 32 | 16 | 8 | 4 | 2 | 1 | 0.5 | 0.25 | 0.125 | 0.063 | 0.031 | 0 | µg/ml Zidovudine |
| Meropenem 612 | 0.05 | 0.05 | 0.05 | 0.04 | 0.04 | 0.04 | 0.05 | 0.04 | 0.05 | 0.05 | 0.05 | 0.05 | 2 |
| 256 | 0.05 | 0.04 | 0.04 | 0.04 | 0.04 | 0.04 | 0.04 | 0.04 | 0.04 | 0.05 | 0.04 | 0.05 | |
| 128 | 0.05 | 0.04 | 0.04 | 0.04 | 0.05 | 0.05 | 0.05 | 0.05 | 0.05 | 0.05 | 0.05 | 0.05 | |
| 64 | 0.05 | 0.04 | 0.04 | 0.04 | 0.04 | 0.05 | 0.04 | 0.05 | 0.05 | 0.05 | 0.05 | 0.05 | |
| 32 | 0.04 | 0.04 | 0.04 | 0.04 | 0.04 | 0.04 | 0.05 | 0.04 | 0.04 | 0.04 | 0.05 | 0.05 | |
| 16 | 0.04 | 0.04 | 0.04 | 0.04 | 0.04 | 0.05 | 0.05 | 0.05 | 0.05 | 0.05 | 0.05 | 0.05 | |
| 8 | 0.05 | 0.04 | 0.04 | 0.04 | 0.05 | 0.05 | 0.05 | 0.05 | 0.05 | 0.05 | 0.05 | 0.05 | |
| 0 | 0.05 | 0.05 | 0.04 | 0.04 | 0.05 | 0.05 | 0.05 | 0.05 | 0.05 | 0.40 | 0.06 | 0.08 | |

From these chequerboards the MIC of meropenem was calculated to be 256 µg/ml and the MIC for colistimethate sodium (CMS) was 32 µg/ml. When zidovudine was added at 0.25 µg/ml to the meropenem and CMS combination, MIC of meropenem remained the same but CMS MIC was reduced to 8 µg/ml. When zidovudine was added at 0.5 µg/ml to the meropenem and CMS combination, MIC of meropenem was reduced to 64 µg/ml and CMS MIC was reduced to 0.5 µg/ml. When zidovudine was added at 1 µg/ml to the meropenem and CMS combination, MIC of meropenem was reduced to 16 µg/ml and CMS MIC was reduced to 0.25 µg/ml. This significant reduction of MIC for both meropenem and CMS is indicative of synergy between the zidovudine and both meropenem and CMS.

Example 4: In Vitro Synergistic Effect of Zidovudine in Combination with Meropenem and CMS Against Log Phase NDM-1 *Klebsiella pneumoniae* Subsp. *Pneumoniae*

The objective of this example was to test the synergistic effect of zidovudine, meropenem and colistin (in the form of CMS) in combination against log phase NDM-1 *K. pneumoniae* subsp. *pneumoniae* (BAA2470) by time-kill methods over a time period of 24 hours.

Materials and Methods
1. Bacterial strain used: BAA2470 strain of *K. pneumoniae* subsp. *pneumoniae*
2. Growth of bacteria: Log phase growth of BAA2470 was carried out according to known methods in the art, e.g. SOP R-005-00 Log Phase Growth of Bacteria.
3. Compound preparation: zidovudine, mereopenem and colistimethate sodium were obtained from commercial sources (e.g. Sigma-Aldrich).
4. The overnight culture was diluted with nutrient broth (Oxoid) to $10^7$ CFU/ml and 280 µl and 290 µl of the culture was added to each combination well and drug respectively, to make the final concentration of 300 µl.
5. Incubation of the compounds with the bacterial suspension was carried out for 24 hours. At 0, 2, 4, 7 and 24 hours, CFU counts were performed to measure the kill effects of the drug combination.

RESULTS AND DISCUSSION

Figure 3:
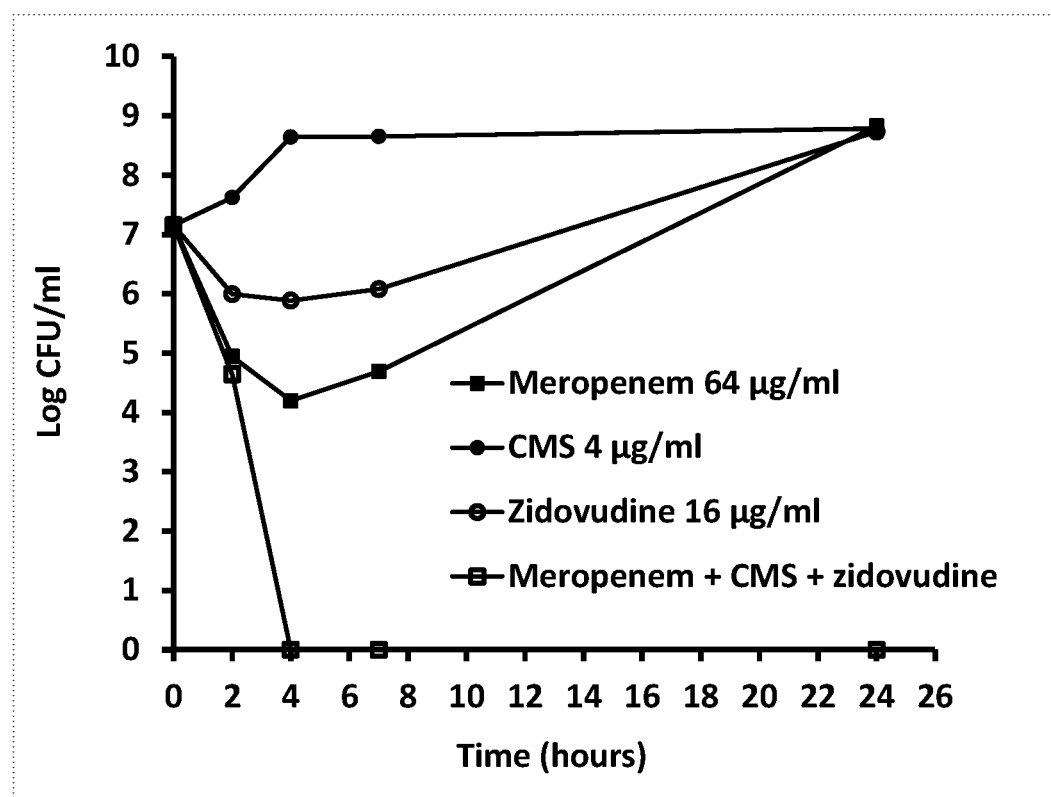
FIG. 3 is a time-kill curve (Log CFU/ml against time (hours)) showing the antimicrobial activity of meropenem at a concentration of 64 µg/ml, colistimethate sodium (CMS) at a concentration of 4 µg/ml, zidovudine at a concentration of 16 µg/ml, and the triple combination of meropenem (64 µg/ml), zidovudine (16 µg/ml) and CMS (4 µg/ml) against log phase NDM-1 *K. pneumoniae* subsp. *pneumoniae* (BAA2470).

The results are shown in FIG. 3 where it can be seen that meropenem used alone at 64 µg/ml killed about 3 logs of the bacterium at 4 hours followed by a regrowth; zidovudine at 16 µg/ml killed one log of the bacterium at 2 hours then growth occurred; CMS at 4 ug/ml showed no effect against the bacterium; and yet the triple combination of colistin, meropenem and zidovudine showed fast kill and achieved complete long-term kill of the bacterium at 4 hours. In view of the lack of activity for each of the drugs alone, the synergy seen for the triple combination according to the claimed invention is a surprising and advantageous technical effect for the treatment of microbial infections.

The invention claimed is:
1. A combination comprising zidovudine or a pharmaceutically acceptable salt and/or solvate thereof and a carbapenem or a pharmaceutically acceptable salt and/or solvate thereof, wherein the combination optionally further comprises at least one polymyxin selected from polymyxin B or polymyxin E, or at least one pharmaceutically acceptable salt and/or solvate thereof.
2. The combination according to claim 1, wherein the carbapenem is selected from the group consisting of imipenem, meropenem and ertapenem or a pharmaceutically acceptable salt and/or solvate thereof.
3. The combination according to claim 1, wherein the carbapenem is meropenem or a pharmaceutically acceptable salt and/or solvate thereof.
4. The combination according to claim 1, wherein the combination includes at least one polymyxin selected from polymyxin B and polymyxin E, or at least one pharmaceutically acceptable salt and/or solvate of each.

5. The combination according to claim 4, wherein the at least one polymyxin is polymyxin E or a pharmaceutically acceptable salt and/or solvate thereof.

6. A method for treating a microbial infection which comprises administering to a mammal, including man, zidovudine or a pharmaceutically acceptable salt and/or solvate thereof in combination with a carbapenem or a pharmaceutically acceptable salt and/or solvate thereof, optionally with a polymyxin selected from polymyxin E and polymyxin B, or a pharmaceutically acceptable salt and/or solvate thereof.

7. The method according to claim 6, wherein the microbial infection is a bacterial infection.

8. The method according to claim 7, wherein the bacterial infection is caused by *E. coli* or *Klebs. pneumoniae*.

9. The method according to claim 7, wherein the infection is caused by a drug-resistant strain of the bacteria.

10. A pharmaceutical composition comprising zidovudine or a pharmaceutically acceptable salt and/or solvate thereof in combination with a carbapenem or a pharmaceutically acceptable salt and/or solvate thereof, wherein the pharmaceutical composition optionally further comprises at least one polymyxin selected from polymyxin B or polymyxin E, or at least one pharmaceutically acceptable salt and/or solvate thereof, and wherein the pharmaceutical composition contains a pharmaceutically acceptable adjuvant, diluent or carrier.

11. The pharmaceutical composition according to claim 10, wherein the carbapenem is meropenem or a pharmaceutically acceptable salt and/or solvate thereof.

12. The pharmaceutical composition according to claim 10, wherein the pharmaceutical composition includes at least one polymyxin selected from polymyxin B and polymyxin E, or a pharmaceutically acceptable salt and/or solvate thereof.

13. The pharmaceutical composition according to claim 12, wherein the at least one polymyxin is polymyxin E or a pharmaceutically acceptable salt and/or solvate thereof.

* * * * *